(12) United States Patent
Jacquot et al.

(10) Patent No.: US 9,382,182 B2
(45) Date of Patent: Jul. 5, 2016

(54) PROCESS FOR PREPARING DIACID COMPOUNDS

(71) Applicant: RHODIA OPERATIONS, Paris (FR)

(72) Inventors: Roland Jacquot, Francheville (FR); Bouchra Rhers, Mistral (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/415,491

(22) PCT Filed: Jun. 26, 2013

(86) PCT No.: PCT/EP2013/063363
§ 371 (c)(1),
(2) Date: Jan. 16, 2015

(87) PCT Pub. No.: WO2014/012754
PCT Pub. Date: Jan. 23, 2014

(65) Prior Publication Data
US 2015/0175515 A1    Jun. 25, 2015

(30) Foreign Application Priority Data
Jul. 19, 2012    (FR) ...................................... 12 56996

(51) Int. Cl.
*C07C 51/00* (2006.01)
*C07C 51/42* (2006.01)
*C07C 51/44* (2006.01)

(52) U.S. Cl.
CPC ................. *C07C 51/00* (2013.01); *C07C 51/42* (2013.01); *C07C 51/44* (2013.01)

(58) Field of Classification Search
None
See application file for complete search history.

(56) References Cited

U.S. PATENT DOCUMENTS

| 3,931,243 A | 1/1976 | Paustian et al. |
| 2009/0326261 A1* | 12/2009 | Leconte ................. C07C 67/20 560/129 |
| 2010/0292121 A1* | 11/2010 | Jacquot et al. ............... 510/245 |

FOREIGN PATENT DOCUMENTS

FR    2993559 B1    8/2014

OTHER PUBLICATIONS

Database Caplus Chemical Abstracts Service, Columbus, Ohio, US; Database Accession No. 1953:9076, Abstract of Salmon-Legagneur, Compt. rend. (1952), 234, 1060.*
March "Aliphatic Nucleophilic Substitution" in Advanced Organic Chemistry,1985, 338-339, John Wiley 8 Sons, New York.*
"Maleic Anhydride, Maleic Acid, and Fumaric Acid" in Kirk-Othmer Encyclopedia of Chemical Technology, Timothy R. Felthouse, Published Online : Oct. 18, 2001.*
"Succinic Acid and Succinic Anhydride" in Kirk-Othmer Encyclopedia of Chemical Technology, Fumagalli et al., Published Online: Apr. 14, 2006, Copyright © 2001 John Wiley & Sons, Inc., pp. 1-20.*
"March, Aliphatic nucleophil substitution, "Advanced Organic Chemistry",1985, 338-339, John Wiley 8 Sons, New York, XP002694107,ISBN: 0-471-88841-9".
F. A. Carey "Organic Chemistry", 1987, McGraw-Hill, Inc., section 21.2 (pp. 777-780).

* cited by examiner

*Primary Examiner* — Karl J Puttlitz

(57) ABSTRACT

The present invention relates to a process for preparing at least one diacid compound, comprising a step of hydrolysis reaction of at least one imide compound, performed in the absence of catalyst.

20 Claims, No Drawings

PROCESS FOR PREPARING DIACID COMPOUNDS

This application is a U.S. national stage entry under 35 U.S.C. §371 of International Application No. PCT/EP2013/063363, filed Jun. 26, 2013, which claims priority to French Application No. 1256996 filed on Jul. 19, 2012. The entire content of each of these applications is hereby incorporated herein.

The present invention relates to a process for preparing diacid compounds.

The invention relates more particularly to a process for preparing diacid compounds using a hydrolysis reaction.

The invention relates even more particularly to a process for preparing branched diacid compounds such as 2-methylglutaric acid (also known as MGA) and 2-ethylsuccinic acid (also known as ESA).

MGA has a promising future in the chemical industries sector. It is a mixture bearing functionalities that can replace adipic acid, which is used for the preparation of Nylon. It may be used as a replacement for adipic acid, as a monomer for the preparation of polyurethanes, plasticizers and detergents, or as a solvent.

It is known practice to prepare diacid compounds by hydrolysis of dinitrile compounds in the presence of an excess of basic hydroxyl compounds, the carboxylate salt obtained then being reacted with a mineral acid to recover the diacid compound.

It is also known practice to prepare diacid compounds by hydrolysis of dinitrile compounds in the presence of an excess of strong mineral acid.

Besides the fact that they use a large amount of reagents, these processes have the drawback of producing a large amount of non-upgradeable by-products, which then need to be processed and destroyed.

The search is ongoing for an improved process for preparing diacid compounds that does not have the abovementioned drawbacks.

One of the aims of the present invention is to propose a process for preparing diacid compounds at a degree of conversion and in a yield equivalent, if not superior, to those of the processes of the prior art, and which is easy to perform and inexpensive on an industrial scale.

Another aim of the present invention is to propose a process that does not generate substantial amounts of effluents or by-products that are harmful to the environment.

Another aim of the invention is to propose a process in which the co-products are readily recoverable and upgradeable.

Another aim of the present invention is to propose a clean process for upgrading the co-products of butadiene hydrocyanation.

To this end, a subject of the invention is a process for preparing at least one diacid compound, comprising a step of hydrolysis of at least one imide compound.

The present invention relates to a process for preparing at least one diacid compound, comprising a step of hydrolysis reaction of at least one imide compound, performed in the absence of catalyst.

In a reaction A→B, the degree of conversion τ(A) of a reagent A at the end of a reaction is defined by the ratio of the difference between the number of moles of A initially introduced $n_0(A)$ and the number of moles of A remaining $n(A)$ at the end of the reaction, to the number of moles of A initially introduced $n_0(A)$:

$$\tau(A) = \frac{n_0(A) - n(A)}{n_0(A)}$$

In a reaction A→B, the yield η(B) of a product B at the end of a reaction is defined by the ratio of the number of moles of B formed $n(B)$ at the end of the reaction to the number of moles of reagent A initially introduced $n_0(A)$:

$$\eta(B) = \frac{n(B)}{n_0(A)}$$

In a reaction A→B, the selectivity S(B) of a product B at the end of a reaction is defined by the ratio of the number of moles of B formed $n(B)$ at the end of the reaction to the number of moles of limiting reagent A consumed $n_0(A) - n(A)$:

$$S(B) = \frac{n(B)}{n_0(A) - n(A)}$$

In the context of the present patent application, the term "diacid compound" means an organic chemical compound comprising two carboxylic acid functions (—C(O)OH). The diacid compounds are preferably $C_4$-$C_{20}$ compounds. Within the same compound, the two carboxylic acid functions are preferably separated by at least two carbon atoms and typically two or three carbon atoms. In other words, the two carboxylic acid functions are not borne by the same carbon atom.

The diacid compound is optionally in the form of ammonium monocarboxylate on account of the presence of ammonia derived from the hydrolysis reaction in the reaction medium.

Such compounds are especially useful as monomers for the preparation of polyurethanes.

In the context of the present patent application, the term "imide compound" means a heterocyclic organic chemical compound comprising a cyclic imide function (—C(O)—NH—C(O)—), i.e. an imide function which is included in a ring. The imide compounds are preferably $C_4$-$C_{20}$ compounds. Preferably, the heterocyclic ring of the imide compounds consists of carbon atoms, typically from 2 to 12, and of the nitrogen atom of the imide function.

According to one embodiment, the imide compound is a compound or a mixture of compounds of general formula (I) below:

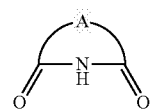
(I)

and the diacid compound is a compound or a mixture of compounds of general formula (II) below:

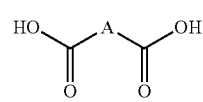
(II)

in which the radical -A- represents a linear or branched, saturated or unsaturated divalent hydrocarbon-based radical comprising from 2 to 12 carbon atoms.

The radical -A- is typically a divalent alkylene group comprising on average at least 2 carbon atoms, preferably from 2 to 6, advantageously from 2 to 4 and preferentially 4 carbon atoms.

The imide compound is, for example, a mixture of different compounds of formula (I), in which the various radicals -A- are preferably isomeric radicals comprising an identical number of carbon atoms.

The use of mixtures of compounds of formula (I) may prove to be advantageous in the context of certain uses of the process.

Thus, the process of the invention may be performed using a single imide compound or a mixture of imide compounds, which may or may not be isomers.

Preferably, the radical -A- is branched. Preferably, the radical -A- is saturated.

According to another embodiment, the radical -A- is linear.

According to another embodiment, the radical -A- is unsaturated.

Preferably, the radical -A- is an unsubstituted hydrocarbon-based radical, i.e. a radical consisting solely of carbon and hydrogen atoms.

According to one embodiment, the radical -A- is a linear alkyl chain substituted with side groups comprising heteroatoms, such as nitrogen, oxygen or sulfur atoms. The radical -A- may be substituted with one or more side groups chosen from the group formed by —CN, —OH, —O($C_1$-$C_6$)alkyl, phenyl and —Ophenyl groups and halogens.

According to one embodiment, the radical -A- represents a saturated divalent hydrocarbon-based radical comprising from 2 to 6 carbon atoms, especially a $C_2$-$C_6$ alkylene radical, preferably of general formula —$C_4H_8$—, which is preferably branched.

According to this embodiment, the radical -A- is preferably chosen from the group consisting of —$CH_2$—$CH_2$—CH($CH_3$)— and —$CH_2$—CH($CH_2CH_3$)— radicals.

According to one embodiment, the process of the invention may be performed using 2-methylglutarimide, 2-ethylsuccinimide and mixtures thereof.

According to this embodiment, 2-methylglutaric acid, 2-ethylsuccinic acid and mixtures thereof, respectively, are obtained.

It is especially possible to use a material composition comprising branched imide compounds, more particularly:
from 70 mol % to 95 mol % and preferably from 75 mol % to 90 mol % of 2-methylglutarimide,
from 5 mol % to 30 mol % and preferably from 5 mol % to 20 mol % of 2-ethylsuccinimide.

According to one embodiment, the starting imide of formula (I) is 2-methylglutarimide (MGI) obtained from methylglutaronitrile (MGN) or from a mixture of dinitriles derived from the process for manufacturing adiponitrile via double hydrocyanation of butadiene. This mixture preferably corresponds to the distillation fraction for separating branched dinitriles (2-methylglutaronitrile and 2-ethylsuccinonitrile) from adiponitrile.

This mixture of dinitriles generally has the following composition by weight:
2-methylglutaronitrile: between 70% and 95% and preferably from 80% to 85%;
2-ethylsuccinonitrile: between 5% and 30% and preferably from 8% to 12%; and
adiponitrile: between 0% and 10% and preferably from 1% to 5%,
the remainder to 100% corresponding to various impurities.

The starting imide compound of formula (I), especially when it is 2-methylglutarimide (MGI), may be obtained from 2-methylglutaronitrile (MGN) or from a mixture of dinitriles as described above, for example via a process of reaction of MGN or of the mixture of dinitriles with an acid. It may also be obtained via a process of hydrolysis of MGN or of the mixture of dinitriles, in the presence of water and of a catalyst, for example of titanium oxide type.

According to one embodiment, typically starting with said material composition, the process of the invention makes it possible to obtain 2-methylglutaric acid, 2-ethylsuccinic acid, and also mixtures thereof.

According to one embodiment, the radical -A- represents an unsaturated divalent hydrocarbon-based radical comprising from 2 to 6 carbon atoms, preferably chosen from the group consisting of an ethylenyl radical and an o-phenylene radical.

The term "ethylenyl radical" means a radical of formula:

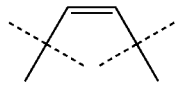

The term "o-phenylene radical" means a radical of formula:

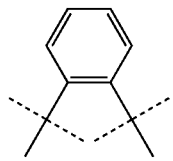

According to one embodiment, the process of the invention is performed using maleimide or phthalimide.

According to this embodiment, the process of the invention makes it possible to obtain, respectively, maleic acid and phthalic acid.

The invention also relates to the products, including the material compositions, which may be obtained, or obtained directly, via this process. The invention also relates to the use of these products or material compositions, especially as solvents, cosolvents, monomers and synthetic intermediates.

According to the invention, the imide compounds are hydrolyzed to diacid compounds by reaction with water molecules. The diacid compounds are said to be the products of hydrolysis of the imide compounds.

More specifically, the starting imide compounds are hydrolyzed to diacid compounds by hydrolysis of the imide functions of the imide compounds. Hydrolysis of the imide function brings about opening of the heterocyclic ring of the imide compounds.

Thus, the carbon atoms of the two carboxylic acid functions of each diacid compound correspond to the carbon atoms of the imide function of the corresponding imide compound.

During the hydrolysis reaction of the imide compound and the opening of the heterocyclic ring, an ammonia molecule is formed.

Schematically, the hydrolysis reaction of an imide compound to a diacid compound in the process of the invention may be represented in the following manner:

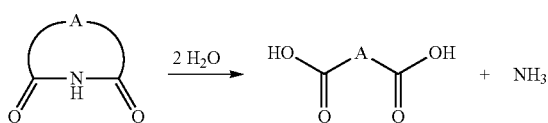

In the reaction medium, the diacid compound obtained is optionally in the form of ammonium monocarboxylate:

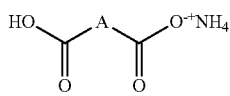

The hydrolysis reaction step of the process of the invention is essentially performed in the presence of water, preferably solely in the presence of water.

The hydrolysis reaction step of the process of the invention is performed in the absence of catalyst.

According to the invention, the imide compounds are hydrolyzed to diacid compounds without said imide compounds being in the presence of any catalyst, of whatever amount. Thus, no homogeneous catalyst or heterogeneous catalyst, supported on a particulate material or on a fixed bed, is used.

In the context of the present patent application, the term "catalyst" means a compound which accelerates a chemical reaction, for instance a hydrolysis reaction.

For the purposes of the present patent application, a catalyst is used in substoichiometric amount relative to the reagents (typically less than 5 mol %).

It may be an acidic or basic catalyst.

The term "acidic catalyst" means an acidic catalyst within the Lewis acid meaning, as defined in the literature, especially by Jerry March, *Advanced Organic Chemistry*, 3rd edition, John Wiley & Sons, 1985, pp. 227 et seq.

The term "basic catalyst" means a basic catalyst within the Lewis base meaning, as defined in the literature, especially by Jerry March, *Advanced Organic Chemistry*, 3rd edition, John Wiley & Sons, 1985, pp. 227 et seq.

The term "catalyst" especially means a heterogeneous catalyst based on alkali metal, alkaline-earth metal and/or lanthanide hydroxides and/or oxides. It may especially be alumina, titanium oxide, magnesia (MgO), $Mg(OH)_2$, CaO, $Ca(OH)_2$, BaO, $Ba(OH)_2$, heteropolyacids, zeolites of pentasil and faujasite type, clays, metal phosphates, silica/alumina mixtures and the like. It may in particular be a catalyst chosen from alkaline-earth metal and/or rare-earth metal oxides, hydroxides and basic salts not having a valency state IV, and from minerals containing same.

The term "acidic catalyst" also means an aqueous solution of a strong acid, such as an aqueous solution of hydrochloric acid, sulfuric acid or nitric acid.

The term "basic catalyst" also means an aqueous solution of a strong base, such as a sodium hydroxide or potassium hydroxide solution.

The inventors have discovered, surprisingly, that a hydrolysis reaction of an imide compound to a diacid compound does not require the presence of a catalyst. The inventors have discovered, even more surprisingly, a process not using a catalyst, which makes it possible to obtain a degree of conversion, a yield and a reaction time equivalent to those of a process using a catalyst.

According to one embodiment, another advantage of the process according to the invention is that it does not generate any salts, which usually need to be separated out, processed and destroyed.

Specifically, according to this embodiment, the ammonia formed by the hydrolysis of the imide compound may be removed in gaseous form gradually as it is formed and/or at the end of the reaction, by distillation. This particular aspect of the process will be detailed later.

According to one embodiment, the process according to the invention comprises, before the hydrolysis reaction step, a step of placing at least one imide compound in contact with water to obtain a mixture of the imide compound and water.

The starting reagents for the hydrolysis reaction are thus placed in contact. Preferably, the only reagents placed in contact are the imide compound (or a mixture of imide compounds) and water.

The step of placing in contact may consist in preparing a mixture comprising water and the imide compound.

The water acts both as solvent and as reagent.

The hydrolysis reaction of the process according to the invention is typically performed in a reactor, which is pre-filled with at least one imide compound and water, which constitute the reaction medium of the hydrolysis reaction of the process of the invention.

This mixture may be prepared in the reactor, or alternatively outside the reactor and then introduced into the reactor.

The placing in contact of the imide compound and water is generally performed at the start of the process.

Alternatively, according to one embodiment, the placing in contact of the imide compound and water may be continued during the hydrolysis reaction, especially in the case of the process in a continuous regime. In this case, the imide compound and/or the water are introduced continuously into the reactor.

According to one embodiment, after the step of placing in contact, the mole ratio between the water and the imide compound is from 10 to 100, preferably from 15 to 30, and preferably equal to about 20.

Said mole ratio corresponds to the ratio of the amount of water (in moles) to the amount of imide compound (in moles) introduced into the reactor.

The above mole ratio ranges make it possible to obtain degrees of conversion of the imide compounds into diacid compounds, which are similar to those of the prior-art processes with a catalyst.

The optimum degree of conversion is obtained when the mole ratio is more particularly from 15 to 30 and preferably equal to about 20.

According to one embodiment, the hydrolysis reaction step of the process of the invention is performed at a temperature of from 160° C. to 220° C.

According to one embodiment, the reaction medium in which the hydrolysis reaction of the imide compound to the diacid compound takes place is raised to a temperature of from 160° C. to 220° C. This heating of the reaction medium may be performed by any means known in the field, such as electrical heating or heating with a heat-exchange fluid.

Heating of the reaction medium makes it possible to accelerate the hydrolysis reaction and to reduce the time required to obtain the diacid compound.

According to one embodiment, the temperature is preferably from 170° C. to 200° C. and preferably equal to about 180° C.

The above temperature ranges make it possible to obtain degrees of conversion of the imide compounds into diacid compounds, which are similar to those of the prior-art processes with a catalyst.

The optimum degree of conversion is obtained when the temperature is more particularly from 170° C. to 200° C. and preferably equal to about 180° C.

The embodiments of the process according to the invention described above make it possible to obtain a high degree of conversion and/or high selectivity, and/or to limit the formation of unwanted byproducts.

The hydrolysis reaction step is typically performed in the liquid phase.

This means that the reaction medium remains liquid during this step.

When the hydrolysis reaction is performed by heating, a pressure is generated especially by evaporation of the water.

Preferably, the hydrolysis reaction is performed at a pressure of from 1 to 50 bar and preferably at the autogenous pressure, i.e. the pressure in the reactor is generated solely by the heating of the reaction medium.

According to one embodiment, the reactor is equipped with a means for monitoring and regulating the pressure, such as a valve via which steam and other compounds in gaseous form escape, especially such as the ammonia formed.

The process of the invention may be performed in a closed system, i.e. without exchange of matter between the interior and the exterior of the reactor during the reaction.

The process of the invention may be performed in an open system, i.e. an exchange of matter between the interior and the exterior of the reactor is allowed during the reaction, typically via a pressure regulation means or by occasional opening of the reactor.

According to the process of the invention, the duration of the hydrolysis reaction step is generally from 30 minutes to 6 hours and preferably from 2 hours to 4 hours.

The process of the invention makes it possible to obtain a satisfactory degree of conversion with a reaction time equivalent to that of the prior-art processes using a catalyst.

During the hydrolysis reaction of the imide compound, ammonia is formed.

The process of the invention is preferably performed in an open system, enabling removal of the ammonia.

Specifically, in a closed system, the ammonia does not get removed from the reaction medium and the diacid compound formed is predominantly found in the form of ammonium monocarboxylate dissolved in the water:

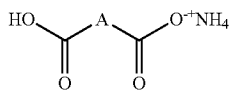

According to an advantageous embodiment of the invention, the proportion of ammonium monocarboxylate obtained after the process is reduced.

As will be seen hereinbelow, according to an advantageous embodiment, it is possible to convert the ammonium monocarboxylate into the diacid form by subsequent distillation of the ammonia.

According to one embodiment of the process of the invention, the ammonia produced by the hydrolysis reaction is removed from the reaction medium, continuously or occasionally and optionally repeatedly.

The advantage of this embodiment is that it reduces the ammonia concentration in the medium and promotes the hydrolysis reaction by shifting the equilibrium.

Furthermore, this reduces the proportion of diacid compound in ammonium monocarboxylate form and increases the proportion of diacid compound in acid form.

According to one variant of the invention, the ammonia is removed by entrainment with water vapor.

According to this variant, the ammonia is withdrawn from the reactor in gaseous form by entrainment with water vapor. This variant makes it possible to remove the ammonia continuously.

The ammonia may especially be withdrawn using a suitable device that enables the pressure to be kept constant, leaving the gas to escape when the pressure exceeds a certain value, and enabling, where appropriate, liquefaction after the escape. This device may be separated from the reactor by a pipe.

The removal of the ammonia may be accompanied by a simultaneous removal of water also in gaseous form. It is preferably sought to limit the simultaneous removal of water. To this end, it is possible, for example, to cool the gases along a pipe separating the device reactor, so as at least partially to liquefy the water and to feed it back into the reactor. The gas(es) removed may be recovered and reused, where appropriate after separating out the ammonia and the water. After separation, the water may be reused for performing the hydrolysis step. Water may also be reinjected continuously into the reactor to renew the water which evaporates off and entrains the ammonia.

According to another variant, the ammonia is removed by stripping with nitrogen.

"Stripping with nitrogen" means flushing with nitrogen, i.e. a step during which a stream of nitrogen under pressure is passed through the reactor in which the hydrolysis reaction takes place, in order to entrain the ammonia in gaseous form. The term "through the reactor" means in the reactor headspace and/or in the reaction medium. This is in a way a gas/liquid extraction.

This step of stripping with nitrogen may be performed one or more times during the process, and preferably at least twice.

Alternatively, typically in the context of performing the process in an open system, the stripping with nitrogen may be performed continuously during the hydrolysis reaction by regulating the flow of nitrogen injected into the reaction medium.

The ammonia thus removed in gaseous form is advantageously recovered by condensation, and may thus be upgraded.

The ammonia removed may typically be recovered by passing the gases containing the ammonia through a refrigerated pipe.

The recovered ammonia is directly upgraded or may be purified, for example by distillation, to separate out the residual water and to obtain upgradeable ammonia, for example in the processes for preparing nitric acid or hydrogen cyanide.

Once the hydrolysis reaction is complete, the products of hydrolysis of the imide compound are recovered during a step of recovery of the diacid compound formed.

Generally, the reaction mixture comprising the water, the diacid compound(s), optionally partially in ammonium monocarboxylate form, optionally ammonia, and optionally the unreacted imide compound(s) is recovered.

The diacid compounds obtained may be purified via common techniques, for instance treatment on an ion-exchange resin, treatment with active charcoal, distillation, crystallization or liquid/liquid extraction.

The diacid compounds generally have a relatively high boiling point, greater than 300° C. The boiling point of MGA at 1 atmosphere is especially 320° C.

The diacid compounds obtained are preferably purified during a distillation step.

This step of purification of the diacid compounds obtained by distillation makes it possible to remove in gaseous form all or part of the compounds that are not diacid compounds, such as the water, the unreacted reagents, and also byproducts of the hydrolysis reaction, especially such as the ammonia formed.

This step also makes it possible, by removing the ammonia, to convert the compounds in ammonium monocarboxylate form into compounds in acid form.

The advantage of this step is that it reduces the proportion of compound in ammonium monocarboxylate form and increases the proportion of compound in acid form.

According to one embodiment, the mixture obtained by hydrolysis of the MGI is placed in a boiler equipped with a plate-distillation or packing-distillation column or any other suitable equipment. The system is subjected to a reduced pressure of from 0.1 to 70 mbar, typically 0.7 mbar. The mixture in the boiler is heated to a column head temperature typically of from 140° C. to 200° C. and preferably from 145° C. to 180° C.

The process of the invention may be performed batchwise, in a discontinuous regime or in a continuous regime.

EXAMPLES

The process of the invention will be described in the following examples, which illustrate the invention in a nonlimiting manner.

The analyses were performed by HPLC for the assay of the diacid compounds and of the organic impurities, and by potentiometry and by NMR for the assay of the monocarboxylate and diacid compounds and of the ammonia.

Example 1

Preparation of an MGI/ESI Mixture from an MGN/ESN Mixture

The mixture of imide compounds used in the examples was obtained according to the method described below, starting with a mixture of dinitrile compounds having the following weight composition: 87% of 2-methylglutaronitrile (MGN), 11% of 2-ethylsuccinonitrile (ESN) and 0.5% of adiponitrile (ADN).

1 ml/hour of said mixture of dinitriles and 1 ml/hour of water are coinjected using two syringe pumps onto a catalytic bed composed of 4 ml of titanium oxide (anatase) placed between two layers of 5 ml of glass powder heated to 275° C. and flushed with a stream of 3 l/hour of nitrogen. After reaction for 6 hours, a conversion of the dinitriles of 97% and a yield of imide mixture of 94% are obtained, the mixture having the following weight composition: 85.5% by mass of 2-methylglutarimide (MGI), 10.8% by mass of 2-ethylsuccinimide (ESI), the remainder being organic impurities.

Comparative Example

Influence of the Catalyst on the Hydrolysis Reaction

The mixture of imides of Example 1 (1.0 g) and a large excess of water (50 equivalents of water per 1 equivalent of imides) are successively introduced into a reactor.

A test is performed without catalyst: Example A.

The other tests are performed with a catalyst: Example B with 0.1 g of zeolite 13× catalyst (Zeolyst Hβ) and Example C with 0.1 g of MgO catalyst (Aldrich).

After closing the reactor, it is heated to 200° C. without stirring by shaking.

The headspace is purged while hot (above the boiling point of water) after 1 hour of heating to remove the ammonia formed. The reactor is then heated for a further 2 hours and purged again while hot before cooling fully.

The reaction medium is then filtered, where appropriate, to remove the catalyst and diluted for analysis by HPLC.

The following results are obtained:

|  | τ | η (diacid + monocarboxylate) |
|---|---|---|
| Example A (without catalyst) | 90 | 78 |
| Example B (zeolite 13X) | 55 | 35 |
| Example C (MgO) | 92 | 81 |

With a catalyst of zeolite type, the degree of conversion is poor. When the reaction is performed without catalyst or in the presence of a basic oxide such as MgO, the degree of conversion is greater than 90%.

The test without catalyst gives the same performance as the test with the MgO catalyst.

Example 2

Hydrolysis of MGI to MGA in a Closed System (without Stripping or Steam Entrainment)

Example 2A

The mixture of imide compounds of Example 1 (10.54 g; 80.1 mmol) in water (72.2 ml) is placed in a closed 300 ml autoclave at room temperature. The system is purged 3 times with nitrogen with mechanical stirring.

It is heated for 4 hours at 180° C. at an autogenous pressure of 8 bar.

The reaction mixture is collected at room temperature. The liquid obtained weighs 90.7 g. The water is evaporated off under reduced pressure at 60° C. 17.48 g of a viscous brown mixture are recovered.

This mixture comprises MGA and ESA, in acid form (diacid) and in ammonium salt (monocarboxylate) form.

From the analyses by HPLC and by potentiometry, the degree of conversion is 97% and the yield of diacid+monocarboxylate is 80% (5% diacid and 75% monocarboxylate).

In a closed system, i.e. without any means for removing the ammonia, MGA in carboxylate form is very predominantly obtained.

Example 2B

The mixture of imide compounds of Example 1 (10.55 g; 80.1 mmol) in water (72.1 ml) is placed in a closed 300 ml autoclave at room temperature. The system is purged 3 times with nitrogen with mechanical stirring.

It is heated for 6 hours at 180° C. at an autogenous pressure of 8 bar.

The reaction mixture is collected at room temperature. The liquid obtained weighs 80.04 g. The water is evaporated off under reduced pressure at 60° C. 21.3 g of a viscous brown mixture are recovered.

This mixture comprises MGA and ESA, in acid form (diacid) and in ammonium salt (monocarboxylate) form.

From the analyses by HPLC and by potentiometry, the degree of conversion is 96% and the yield of diacid+monocarboxylate is 84% (7% diacid and 77% monocarboxylate).

In a closed system, i.e. without any means for removing the ammonia, MGA in carboxylate form is very predominantly obtained.

Example 3

Hydrolysis of MGI to MGA with Stripping of the Ammonia with Nitrogen

Example 3A

The mixture of imide compounds of Example 1 (10.55 g; 80.1 mmol) in water (72 ml) is placed in a closed 300 ml autoclave at room temperature. The system is purged 3 times with nitrogen with mechanical stirring.

It is heated for 2 hours at 180° C. at an autogenous pressure of 8 bar. The temperature of the reactor is reduced to 70° C. and nitrogen is circulated in its headspace for 30 minutes to strip out the ammonia.

The heating is resumed for 2 hours, still at 180° C. and at 8 bar. The system is cooled and the ammonia is then stripped out again by circulating nitrogen through for 30 minutes.

The reaction mixture is collected at room temperature. The liquid obtained weighs 77.8 g. The water is evaporated off under reduced pressure at 60° C. 13.5 g of a viscous brown mixture are recovered.

This mixture comprises MGA and ESA, in acid form (diacid) and in ammonium salt (monocarboxylate) form.

From the analyses by HPLC and by potentiometry, the degree of conversion is 93% and the yield of diacid+monocarboxylate is 82.1% (10.6% diacid and 71.5% monocarboxylate).

Example 3B

The mixture of imide compounds of Example 1 (10.4 g; 79.1 mmol) in water (72.5 ml) is placed in a closed 300 ml autoclave at room temperature. The system is purged 3 times with nitrogen with mechanical stirring.

It is heated for 2 hours 30 minutes at 200° C. at an autogenous pressure of 14 bar. The temperature of the reactor is reduced to 70° C. and nitrogen is circulated in its headspace for 30 minutes to strip out the ammonia.

The heating is resumed for 2 hours 30 minutes, still at 200° C. and at 14 bar. The system is cooled and the ammonia is then stripped out again by circulating nitrogen through for 30 minutes.

The reaction mixture is collected at room temperature. The liquid obtained weighs 75.7 g. The water is evaporated off under reduced pressure at 60° C. 12.7 g of a viscous brown mixture are recovered.

This mixture comprises MGA and ESA, in acid form (diacid) and in ammonium salt (monocarboxylate) form.

From the analyses by HPLC and by potentiometry, the degree of conversion is 87% and the yield of diacid+monocarboxylate is 85% (25% diacid and 60% monocarboxylate).

Example 3C

The mixture of imide compounds of Example 1 (10.7 g; 81.4 mmol) in water (71.9 ml) is placed in a closed 300 ml autoclave at room temperature. The system is purged 3 times with nitrogen with mechanical stirring.

It is heated for 3 hours at 180° C. at an autogenous pressure of 8 bar. The temperature of the reactor is reduced to 70° C. and nitrogen is circulated in its headspace for 30 minutes to strip out the ammonia.

The heating is resumed for 3 hours, still at 180° C. and at 8 bar. The system is cooled and the ammonia is then stripped out again by circulating nitrogen through for 30 minutes.

The reaction mixture is collected at room temperature. The green-colored liquid obtained weighs 79.7 g.

This mixture comprises MGA and ESA, in acid form (diacid) and in ammonium salt (monocarboxylate) form.

From the analyses by HPLC and by potentiometry, the degree of conversion is 93% and the yield of diacid+monocarboxylate is 83% (8% diacid and 75% monocarboxylate).

The liquid obtained and recovered is then placed in a boiler equipped with a condenser and a trap, and then distilled at a boiler temperature of 165° C., under a reduced vacuum of 2 mbar.

The contents of the boiler (diacid) and the contents of the trap (ammonium salt) are assayed by potentiometry.

| Fraction | boiler | trap | starting liquid |
| --- | --- | --- | --- |
| mass % of diacids | 82.5 | — | 1.2 |
| mass % of carboxylates | — | 0.44 | 13.1 |

The distillation of a reaction mixture containing water, MGI, MGA and MGA ammonium monocarboxylate makes it possible to convert the MGA ammonium salt into MGA and to remove the ammonia, and also to increase the yield of MGA in diacid form.

Example 4

Hydrolysis of MGI to MGA with Continuous Entrainment of the Ammonia with Water Vapor The mixture of imide compounds of Example 1 (10.6 g; 80.7 mmol) in water (72.6 ml) is placed in a closed 300 ml autoclave at room temperature. The system is purged 3 times with nitrogen with mechanical stirring.

It is heated for 5 hours at 200° C. at an autogenous pressure of 16 bar. Water is added continuously (about 0.5-1 ml/minute) using an HPLC pump.

The ammonia formed is entrained with the water vapor. The water outlet rate is adjusted manually via a micrometric valve. The pressure decreases gently in the course of the test. The ammonia is trapped in a flask containing acidified water and a spatula-tip of phenolphthalein to visualize the passage of the acidic medium to basic.

The reaction mixture is collected at room temperature.

The liquid obtained weighs 124.9 g.

This mixture comprises MGA and ESA, in acid form (diacid) and in ammonium salt (monocarboxylate) form.

From the analyses by HPLC and by potentiometry, the degree of conversion is 96% and the yield of diacid+monocarboxylate is 78% (42% diacid and 36% monocarboxylate).

With continuous entrainment with water vapor, the MGA is obtained in acid form as a mixture with MGA monocarboxylate in equivalent amount.

The amount of ammonia in the reaction mixture and in the trap is also assayed, relative to the amount of starting MGI:

| % NH₃ relative to the MGI introduced | |
|---|---|
| in the reaction mixture | 38.8% |
| in the trap | 55.1% |
| total | 93.9% |

Continuous entrainment with water vapor makes it possible to remove a large amount of ammonia from the reaction medium.

Example 5

Influence of the Stripping with Nitrogen and of the Continuous Entrainment with Water Vapor The results of Examples 2A, 2B, 3A, 3B, 3C and 4 clearly show the influence of the stripping with nitrogen and of the continuous entrainment with water vapor on the yield of diacid compounds:

|  | Closed system | | Stripping with nitrogen Example | | | water continuously |
|---|---|---|---|---|---|---|
|  | 2A | 2B | 3A | 3B | 3C | 4 |
| ζ | 97 | 96 | 93 | 87 | 93 | 96 |
| η (diacid) | 5 | 7 | 10.6 | 25 | 8 | 42 |
| η (monocarboxylate) | 75 | 77 | 71.5 | 60 | 75 | 36 |
| S (diacid + monocarboxylate) | 82.2 | 87.2 | 88.3 | 88.7 | 89.3 | 87.0 |
| Temperature (° C.) | 180 | 180 | 180 | 200 | 180 | 200 |
| Time (hours) | 4 | 6 | 4 | 5 | 6 | 5 |

The high selectivity S (diacid+monocarboxylate) shows that the hydrolysis reaction of the imide compound essentially gives the diacid compound (in diacid form or in monocarboxylate form).

Example 6

Influence of the H₂O/Imides Mole Ratio

Tests were performed, in a closed system, by varying the ratio of the number of moles of water to the number of moles of imide introduced.

|  | Example | | | |
|---|---|---|---|---|
|  | 6A | 6B | 6C | 6D |
| Time (hours) | 4 | 4 | 6 | 4 |
| Temperature (° C.) | 200 | 200 | 200 | 200 |
| Pressure (bar) | 14 | 14 | 14 | 14 |
| n(H₂O)/n(imides) | 50 | 21 | 22 | 9 |
| η (diacid + monocarboxylate) | 81.8 | 82.7 | 84.9 | 64.3 |

The optimum yield is found for a mole ratio equal to about 20.

Example 7

Hydrolysis of MGI to MGA in a Continuous System

An aqueous solution of the mixture of imide compounds of Example 1 at 16% by mass is continuously introduced, at a flow rate of 0.36 ml/min, into a 20 ml tubular reactor equipped with a heating system via a heat-exchange fluid. The reaction temperature is 210° C. and the reactor outlet pressure is adjusted to 20 bar. The residence time at this temperature is about 1 hour.

From the analyses by HPLC and by potentiometry, the degree of conversion is 90% and the yield of diacid+monocarboxylate is 83% (17% diacid and 66% monocarboxylate).

Example 8

Hydrolysis of Succinimide to Succinic Acid in a Closed System 0.71 g of succinimide (Aldrich) and 6.0 g of water are placed in a 10 ml closed autoclave at room temperature. It is heated for 4 hours at 200° C. at the autogenous pressure.

The reaction mixture is collected at room temperature. The brown liquid obtained weighs 6.21 g. The water is evaporated off under reduced pressure at 60° C.

This mixture essentially comprises succinic acid in ammonium salt (monocarboxylate) form.

From the analyses by HPLC and by potentiometry, the degree of conversion is 91% and the selectivity toward monocarboxylate is 96%.

Example 9

Hydrolysis of Phthalimide to Phthalic Acid in a Closed System 1.01 g of phthalimide (Aldrich) and 6.05 g of water are placed in a 10 ml closed autoclave at room temperature. It is heated for 4 hours at 200° C. at the autogenous pressure.

The reaction mixture is collected at room temperature. The mixture obtained weighs 7.06 g. The water is evaporated off under reduced pressure at 60° C.

This mixture essentially comprises phthalic acid in ammonium salt (monocarboxylate) form.

From the analyses by HPLC and by potentiometry, the degree of conversion is 90% and the selectivity toward diacid+monocarboxylate is 92% (2% diacid and 90% monocarboxylate).

The invention claimed is:

1. A process for preparing at least one diacid compound, comprising hydrolyzing, in the absence of any acidic or basic catalyst, at least one imide compound; wherein the step of hydrolyzing is performed at a temperature of from 160° C. to 220° C. and wherein the duration of the step of hydrolyzing is from 30 minutes to 6 hours.

2. The process as claimed in claim 1, wherein the at least one imide compound is a compound or a mixture of compounds of general formula (I) below:

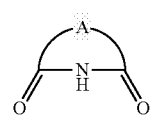

(I)

and the at least one diacid compound is a compound or a mixture of compounds of general formula (II) below:

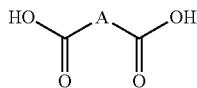

(II)

wherein -A- represents a linear or branched, saturated or unsaturated divalent hydrocarbon-based radical comprising from 2 to 12 carbon atoms.

3. The process as claimed in claim 2, wherein -A- represents a saturated divalent hydrocarbon-based radical comprising from 2 to 6 carbon atoms.

4. The process as claimed in claim 2, wherein -A- represents a divalent hydrocarbon-based radical chosen from the group consisting of —CH$_2$—CH$_2$—CH(CH$_3$)— and —CH$_2$—CH(CH$_2$CH$_3$)— radicals.

5. The process as claimed in claim 2, wherein the at least one imide compound is chosen from the group consisting of 2-methylglutarimide, 2-ethylsuccinimide and mixtures thereof.

6. The process as claimed in claim 2, wherein the at least one diacid compound is chosen from the group consisting of 2-methylglutaric acid, 2-ethylsuccinic acid and mixtures thereof.

7. The process as claimed in claim 2, wherein -A- represents an unsaturated divalent hydrocarbon-based radical comprising from 2 to 6 carbon atoms.

8. The process as claimed in claim 1, further comprising, before the step of hydrolyzing, a step of placing the at least one imide compound in contact with water to obtain a mixture of the at least one imide compound and water.

9. The process as claimed in claim 8, wherein, after the step of placing in contact, the mole ratio between the water and the at least one imide compound is from 10 to 100.

10. The process as claimed in claim 1, wherein the step of hydrolyzing is performed at a temperature from 170° C. to 200°.

11. The process as claimed in claim 1, wherein the step of hydrolyzing produces ammonia, and said ammonia is removed, and then optionally recovered by condensation.

12. The process as claimed in claim 1, further comprising a step of recovering the at least one diacid compound.

13. The process as claimed in claim 1, further comprising a step of purifying the at least one diacid compound by distillation.

14. The process of claim 3, wherein -A- represents a C$_2$-C$_6$ alkylene radical.

15. The process of claim 14, wherein -A- represents a radical of general formula —C$_4$H$_8$—.

16. The process of claim 7, wherein -A- represents a radical chosen from the group consisting of an ethylenyl radical and an o-phenylene radical.

17. The process of claim 9, wherein the mole ratio between the water and the imide compound is from 15 to 30.

18. The process of claim 11, wherein the ammonia is removed by stripping with nitrogen or by entrainment with water vapor.

19. The process as claimed in claim 1, wherein the duration of the step of hydrolyzing is from 4 hours to 6 hours.

20. A process for preparing 2-methylglutaric acid, 2-ethylsuccinic acid, or a mixture thereof, comprising hydrolyzing, in the absence of any acidic or basic catalyst, 2-methylglutarimide, 2-ethylsuccinimide, or a mixture thereof; wherein the step of hydrolyzing is performed at a temperature of from 170° C. to 200° C. and wherein the duration of the step of hydrolyzing is from 4 hours to 6 hours.

* * * * *